US012303703B2

(12) United States Patent
Shaker et al.

(10) Patent No.: US 12,303,703 B2
(45) Date of Patent: May 20, 2025

(54) METHOD OF USING A MEDICAL DEVICE

(71) Applicant: ALTRIX MEDICAL, INC., Centreville, VA (US)

(72) Inventors: Matthew Robert Shaker, Centreville, VA (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

(21) Appl. No.: 18/827,730

(22) Filed: Sep. 7, 2024

(65) Prior Publication Data

US 2025/0082947 A1    Mar. 13, 2025

Related U.S. Application Data

(60) Provisional application No. 63/537,084, filed on Sep. 7, 2023.

(51) Int. Cl.
| | |
|---|---|
| *A61N 1/00* | (2006.01) |
| *A61N 1/04* | (2006.01) |
| *A61N 1/362* | (2006.01) |
| *A61N 1/39* | (2006.01) |

(52) U.S. Cl.
CPC ........... *A61N 1/3904* (2017.08); *A61N 1/046* (2013.01); *A61N 1/0484* (2013.01); *A61N 1/362* (2013.01)

(58) Field of Classification Search
CPC .............................. A61N 1/3904; A61N 1/046
USPC ........................................................... 607/5
See application file for complete search history.

(56) References Cited

U.S. PATENT DOCUMENTS

| | | | |
|---|---|---|---|
| 9,737,701 B2 | 8/2017 | Dupelle et al. | |
| 10,058,247 B2* | 8/2018 | Sagalovich | A61B 8/4477 |
| 11,331,471 B2 | 5/2022 | Andrews et al. | |
| 2011/0276113 A1* | 11/2011 | Cybulski | A61B 18/042 |
| | | | 607/101 |
| 2017/0165114 A1* | 6/2017 | Hallen | A61F 9/00736 |
| 2019/0015657 A1 | 1/2019 | Crutchfield et al. | |
| 2020/0282225 A1 | 9/2020 | Kumar et al. | |
| 2020/0312453 A1 | 10/2020 | Räisänen et al. | |
| 2022/0355122 A1 | 11/2022 | Strommer et al. | |

FOREIGN PATENT DOCUMENTS

| | | | | |
|---|---|---|---|---|
| CA | 3070185 A1 * | 1/2019 | | A61B 6/06 |
| WO | WO-2021181389 A1 * | 9/2021 | | A61B 5/02055 |

* cited by examiner

*Primary Examiner* — Nicole F Lavert
(74) *Attorney, Agent, or Firm* — Louis Ventre, Jr.

(57) ABSTRACT

A method of using a medical apparatus includes a step of providing the medical apparatus. The medical apparatus is hand-held and enables operation of an initial-medical function or initial-state function. The medical apparatus is capable of accepting and operationally integrating into the medical apparatus the contents of an adaptor kit to enable a new medical function. Each adaptor kit includes at least one adaptor-kit cartridge and at least one accessory. Added steps include: using the medical apparatus to perform the initial-medical function or initial-state function; providing a first, a second, and a third adaptor kit to enable the medical apparatus to function as: a wearable automated external defibrillator (AED) with disposable electrode pads; as a wAED with disposable electrode pads; and as a means for taking an electrocardiogram (ECG).

2 Claims, 12 Drawing Sheets

| A method of using a medical apparatus, comprising the steps of: | 100 |

| Providing Step: providing the medical apparatus configured: to be hand-held by a person; to enable use of an initial-medical function for the medical apparatus; and to accept and operationally integrate into the medical apparatus any contents in at least one adaptor kit, wherein the contents of each adaptor kit comprises at least one adaptor-kit cartridge configured to be attached to the medical apparatus, each adaptor-kit cartridge further configured to operationally integrate with the medical apparatus either alone or with another adaptor-kit cartridge; and each adaptor kit further comprises at least one accessory, wherein the adaptor-kit cartridge and the at least one accessory are configured to enable a new medical function for the medical apparatus. | 105 |

| Using Step: using the medical apparatus to perform at least one initial-medical function. | 110 |

| Choosing Step: choosing the initial-medical function from one or more in the group consisting of: taking an electrocardiogram (ECG) of the person; measuring blood pressure within the person; measuring blood composition within the person; measuring body temperature of the person; measuring a heart rate of the person; measuring acceleration of a chest of the person undergoing cardiopulmonary resuscitation (CPR); coaching in delivery of a medical function; performing automated electronic defibrillation of the person; performing at least one pre-programmed self-test of the medical apparatus; updating medical device firmware or software; and providing status information about the medical apparatus. | 115 |

| Selecting Step: selecting the initial-medical function as taking an electrocardiogram (ECG) of the person, identifying a need for an electrocardiogram from the person, the person having bare skin accessible to at least two separated sensors, the at least two separated sensors operationally connected to the medical apparatus; and touching the bare skin to the at least two separated sensors. | 120 |

| Configuring Step: configuring the at least two separated sensors to be functional when the person places a finger on each of the at least two separated sensors. | 125 |

| Supplying Step: providing the medical apparatus with multiple leads for use in taking the ECG. | 130 |

FIG. 1

| A method of using a medical apparatus, the method comprising the steps of: 100 |

| AED Adaptor Step: providing an AED adaptor kit, the AED adaptor kit configured to enable the medical apparatus to perform a second new medical function of a reusable non-wearable automated external defibrillator (AED), the AED adaptor kit comprises: an AED cartridge; and disposable electrode pads. 205 |

| AED Connecting Step: connecting the AED cartridge to the medical apparatus to enable its operation; and placing on the person two of the disposable electrode pads. 215 |

| Storage Step: configuring the AED cartridge to store each of the disposable electrode pads while each such disposable electrode pad is electrically connected to the AED cartridge. 220 |

| wAED Adaptor Step: providing a wAED adaptor kit, the wAED adaptor kit configured to enable the medical apparatus to perform a first new medical function of a wearable automated electronic defibrillator (wAED), the wAED adaptor kit comprises a wAED cartridge configured to attach to, and operationally integrate with, the medical apparatus; and disposable electrode pads. 221 |

| wAED Harness Step: the wAED adaptor kit further comprises a harness and further comprises the step of securing the harness on the person. 222 |

| wAED Implementation Step: connecting the wAED cartridge to the medical apparatus; and attaching the disposable electrode pads to the person. 223 |

| ECG Adaptor Step: providing a ECG adaptor kit, the ECG adaptor kit configured to enable the medical apparatus to perform a third new medical function of taking an electrocardiogram (ECG), the third adaptor kit comprising: an ECG cartridge; and a plurality of sensors configured to measure a magnitude and direction of electrical currents in a heart during each heartbeat. 225 |

FIG. 2

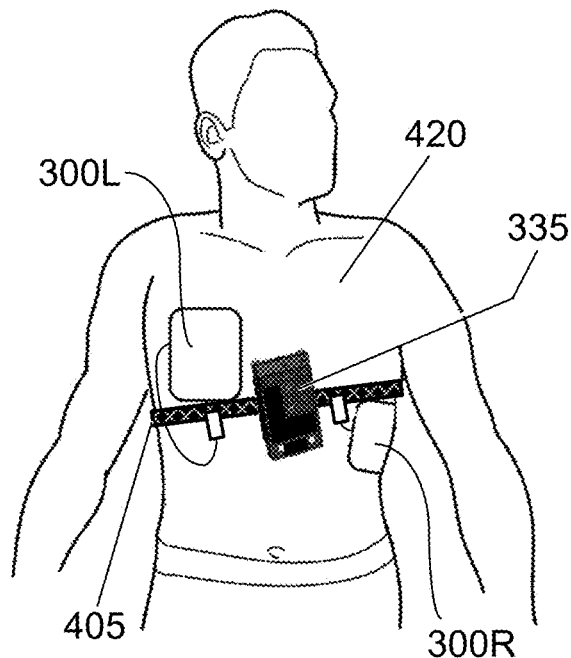
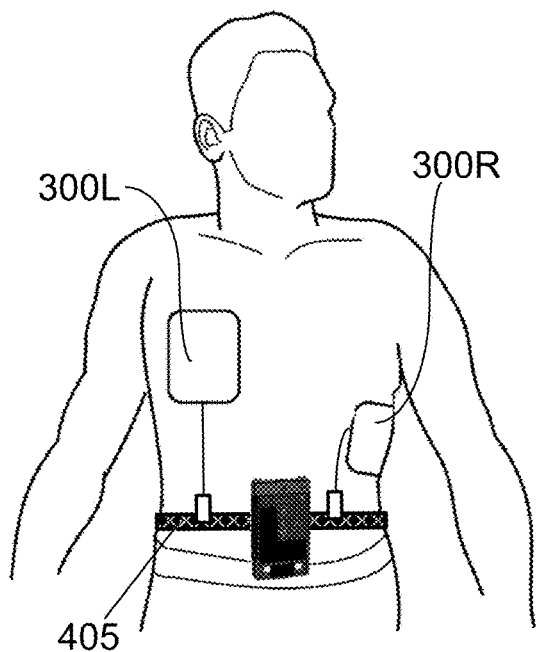
FIG. 4

| A method of using a medical apparatus, comprising the steps of: 1300 |

| wAED Providing Step: providing the medical apparatus configured to perform an initial-state function; the medical apparatus further configured to be modified by the addition of contents of one or more adaptor kits to perform a new medical function; the medical apparatus further configured to be hand-held by a person; and to accept and operationally integrate into the medical apparatus, the contents in a wearable automated electronic defibrillator adaptor kit (wAED adaptor kit); the contents of the wAED adaptor kit comprising a wAED cartridge, a harness and disposable electrode pads; wherein the harness is configured: to be secured on the person; to electrically connect with the disposable electrode pads; and to electrically connect with the medical apparatus; and providing the wAED adaptor kit wherein the wAED cartridge and the harness are configured to be accepted and to be operationally integrated into the medical apparatus and further configured to enable the medical apparatus to perform a new medical function of a wearable automated electronic defibrillator (wAED). 1305 |

| wAED Attaching Step: attaching the wAED cartridge to the medical apparatus; adhering two disposable electrode pads to the person; and electrically connecting the disposable electrode pads to the medical apparatus. 1310 |

FIG. 13

METHOD OF USING A MEDICAL DEVICE

CROSS-REFERENCE TO RELATED APPLICATION

This application claims the benefit of U.S. Provisional Application No. 63/537,084, filed 7 Sep. 2023, which is hereby incorporated by reference herein.

TECHNICAL FIELD

In the field of surgery, a method of using a device for medical evaluation of a condition of a living body, the method involving the detection of heartbeat electric signals and cardiovascular characteristics. Also, in the field of light, thermal, and electrical application, a device for applying electrical energy to the external surface and inside portions of the body to restore normal operation of the heart.

BACKGROUND ART

An automated external defibrillator (AED), is an apparatus designed to be used by a non-medically trained person to help someone who is experiencing a sudden cardiac arrest (SCA). It is designed to deliver an electric charge to the heart in order to restore its normal rhythm. An SCA occurs when the heart's electrical system malfunctions. Such arrythmias cause the heart to stop pumping blood effectively. An AED is designed to detect if a shockable arrythmia is present by using an electrocardiogram (ECG) and, if a shockable arrythmia is present, to provide a therapeutic electric charge.

A person who is at high risk of cardiac arrest will sometimes have an implantable cardioverter-defibrillator (ICD) implanted inside their body to be able to perform defibrillation in the event of SCA. While someone at such risk is waiting for that implantation, the person will often be prescribed a wearable AED (wAED) by their physician. The wAED is a special class of AED that can be worn and may be configured to trigger manually or automatically in the case of an SCA.

Wearable AEDs are prescribed for people who are candidates for an ICD. Such devices are often cumbersome to wear and a patient may discontinue their use because of discomfort. Current technology for a wAED often weighs in excess of 3 pounds. Given the power requirements, a wAED can take up to 16 hours to charge for 12 hours of wear. Both of these factors can be and are improved for wearable AEDs employed using the disclosure herein.

The concept of converting one medical apparatus into a second medical apparatus was first disclosed in patent application Ser. No. 18/343,994 (the '994 patent application), which is hereby incorporated by reference herein. That application disclosed a medical apparatus capable of providing an ECG and also capable of converting to an AED. Disclosed herein is a medical apparatus configured for at least two transformations using adaptor kits. This application effectively describes a hand-held medical apparatus that is physically capable of being converted into at least two additional, distinct and separately functioning medical apparatuses.

SUMMARY OF INVENTION

A method of using a medical apparatus includes an initial step of providing the medical apparatus. The medical apparatus is configured to be hand-held and to enable operation of an initial-medical function for the medical apparatus. It is further configured to accept and operationally integrate into the medical apparatus, the contents or components in one or more adaptor kits needed to convert the medical apparatus to a new medical function. Each adaptor kit at a minimum contains components needed to enable a new medical function for the medical apparatus.

Each adaptor kit includes an adaptor-kit cartridge that attaches to, and operationally integrates with, the medical apparatus. In addition to the adaptor-kit cartridge, each adaptor kit requires use of at least one accessory or component that enables the new medical function. The method may include a step of using the medical apparatus to perform at least one initial-medical function. The initial-medical function is the medical function that is capable of being performed by the medical apparatus before alteration by any adaptor kit.

Exemplary initial-medical functions include taking an electrocardiogram (ECG) of the person; measuring blood pressure within the person; measuring blood composition within the person; measuring body temperature of the person; measuring a heart rate of the person; measuring acceleration of a chest of the person undergoing cardiopulmonary resuscitation (CPR), coaching in delivery of a medical function (e.g., CPR coaching); and performing automated external defibrillation of the person.

The method may include configuring the medical apparatus to: update the medical device firmware or software; to perform at least one pre-programmed self-test of the medical apparatus; and to provide status information about the medical apparatus.

When the initial-medical function is taking an ECG of the person, added steps in the method may include identifying a need for an ECG, then taking the ECG by touching person's bare skin to two separated sensors on the medical apparatus. The at least two separated sensors may be configured to be functional when the person places a finger on each of the separated sensors. The medical apparatus may also be used with multiple leads for use in taking the ECG. While these multiple leads would not be required, such leads are preferably used when provided as optional accessories.

An alternative method includes a step of providing a wAED adaptor kit to enable the medical apparatus to perform a first new medical function of a wearable automated external defibrillator (wAED). The wAED adaptor kit includes a wAED cartridge. Also included in the wAED adaptor kit is an accessory including: a harness configured to be secured around the person. Disposable electrode pads may also be included in the wAED adaptor kit as an accessory. The disposable electrode pads may be included in the wAED adaptor kit, acquired separately, or both included in the wAED adaptor kit and acquired separately, and in either case are made to be compatible with the wAED cartridge. The wAED cartridge may be combined with the harness. In another embodiment, the harness may also be provided separately from the wAED adaptor kit.

The harness is preferably used to secure the medical apparatus on the person and to securely route wires from the disposable electrode pads for connection with the medical apparatus. The alternative method includes steps of attaching the wAED cartridge to the medical apparatus; adhering the disposable electrode pads to the person; connecting the disposable electrode pads either directly to the medical apparatus or indirectly through the wAED cartridge; and securing the harness to the person.

Either the method or the alternative method may include providing an AED adaptor kit to enable the medical apparatus to perform a second new medical function of an automated external defibrillator (AED) configured for use with a plurality of disposable electrode pads included in the AED adaptor kit. The AED adaptor kit preferably includes an AED cartridge that stores at least two disposable electrode pads electrically connected to the AED cartridge.

When the method or the alternative method includes a step of providing an AED adaptor kit, the method further includes steps of connecting the AED cartridge to the medical apparatus to enable AED operation; connecting a left disposable electrode pad and a right disposable electrode pad to the medical apparatus either directly by connecting the AED cartridge; and placing on the person, two of the disposable electrode pads.

Optionally, either the method or the alternative method includes configuring the AED cartridge to store each disposable electrode pad in the plurality of disposable electrode pads in a manner that each such disposable electrode pad is electrically connected to AED cartridge, thereby allowing the left-disposable electrode pad and a right-disposable electrode pad to be connected to the medical apparatus when the AED cartridge is connected to the medical apparatus. Preferably the left and right disposable electrode pads are interchangeable (the left and right designations herein are for discussion purposes only, not for indicating a different physical construction of the disposable electrode pads).

Either the method or the alternative method may include a step of providing an ECG adaptor kit, the ECG adaptor kit enables the medical apparatus to perform a third new medical function of taking an electrocardiogram (ECG), the ECG adaptor kit includes: an ECG cartridge; and a plurality of sensors configured to measure a magnitude and direction of electrical currents in a heart during each heartbeat.

The method and the alternative method include a step of providing a wAED adaptor kit that includes a wAED cartridge and a harness, which are configured to be accepted by, and to be operationally integrated into, the medical apparatus and further configured to enable the medical apparatus to perform a new medical function of a wearable automated external defibrillator (wAED). Additional optional steps include attaching the wAED cartridge to the medical apparatus; adhering two disposable electrode pads to the person; and electrically connecting the disposable electrode pads to the medical apparatus.

BRIEF DESCRIPTION OF DRAWINGS

The drawings illustrate preferred embodiments of a method of using a medical apparatus according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number. Dashed lines used in the drawings indicate optional steps or components and solid lines indicate mandatory steps or components.

FIG. 1 is a chart of showing a mandatory step and five optional steps in the method of using the medical apparatus.

FIG. 2 is a continuation of the chart in FIG. 1 showing six additional optional steps in the method of using the medical apparatus.

FIG. 4 shows two frontal views of a person with two different types of harness securing the medical apparatus with the wAED cartridge and further showing two disposable electrode pads in approximate position for use.

FIG. 13 is a chart of steps for an alternative method providing a medical apparatus convertible to an initial use as a wAED.

DESCRIPTION OF EMBODIMENTS

Figure 3:
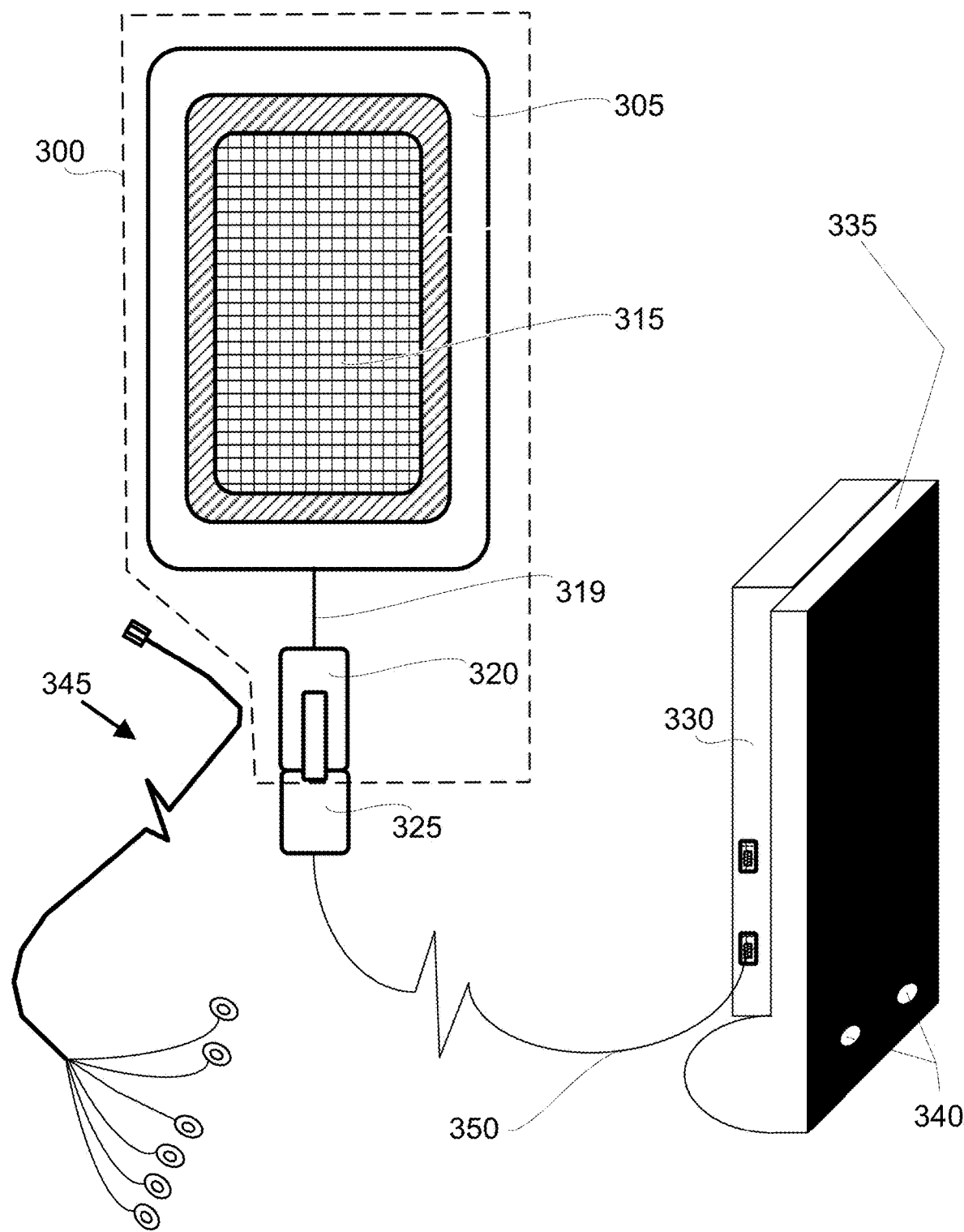
FIG. 3 is a bottom view of a disposable electrode pad, an ECG lead with multiple leads at one end, and a side perspective view of the medical apparatus and a wAED cartridge attached together.

A method (100) is disclosed for using a medical apparatus (335) that is configured to be physically altered and converted to perform an added or different medical function from its initial-medical function. An alternative method (1300) provides for a medical apparatus (335) alterable to a wAED. An initial-medical function is any medical function of the medical apparatus available at the moment the medical apparatus becomes active, whether due to user interaction (such as pressing a button) or an automatic event (such as the device waking from a lower power mode).

The alternative method (1300) starts out with an initial-state function, which is distinguished from the initial-medical function because the initial-state function may be more or less than a medical function (for example, it may be a medical apparatus (335) status (1144), pre-programmed self-test (1143), or provide CPR coaching (1130). Initial-state functions may be initial medical functions, functions required to ensure that medical apparatus is ready and able to execute one or more medical functions, or functions that support medical functions after those functions are complete (a function ready to be triggered to upload ECG data to the cloud upon completion of an ECG). An initial-state function is a medical function or supports one or more medical functions. An initial-state function becomes active, whether due to user interaction (such as pressing a button or upon the device waking from a lower power mode) or an automatic event. Initial state functions may include providing a battery status, providing a status on disposable-electrode pads, performing at least one pre-programmed self-test of the medical apparatus, firmware availability notification, or firmware upgrade.

FIGS. 1, 2 and 13 illustrate the steps in the method (100) and the alternative method (1300). Required steps in these figures are connected by a solid line, and the preferred optional steps, connected by dashed lines, in the disclosed methods of using the medical apparatus (335). The steps may be performed in any sequence or order that complies with the express requirement of a step and that accomplishes the medical function or functions of the method for which the step is performed.

The method (100) of using the medical apparatus (335) includes a Providing Step (105). An alternative method (1300) provides the medical apparatus (335) ready for conversion to a wAED. Optional steps for the method (100) and for the alternative method (1300) include: a Using Step (110); a Choosing Step (115); a Selecting Step (120); a Configuring Step (125); a Supplying Step (130); an AED Adaptor Step (205); an AED Connecting Step (215); a Storage Step (220); a wAED Adaptor Step (221); a wAED Harness Step (222); a wAED Implementation Step (223); and an ECG Adaptor Step (225). For economy of disclosure and convenience, it is intended that the foregoing optional steps for method (100) are also performable for the alternative method (1300), except where expressly noted otherwise.

Figure 10:
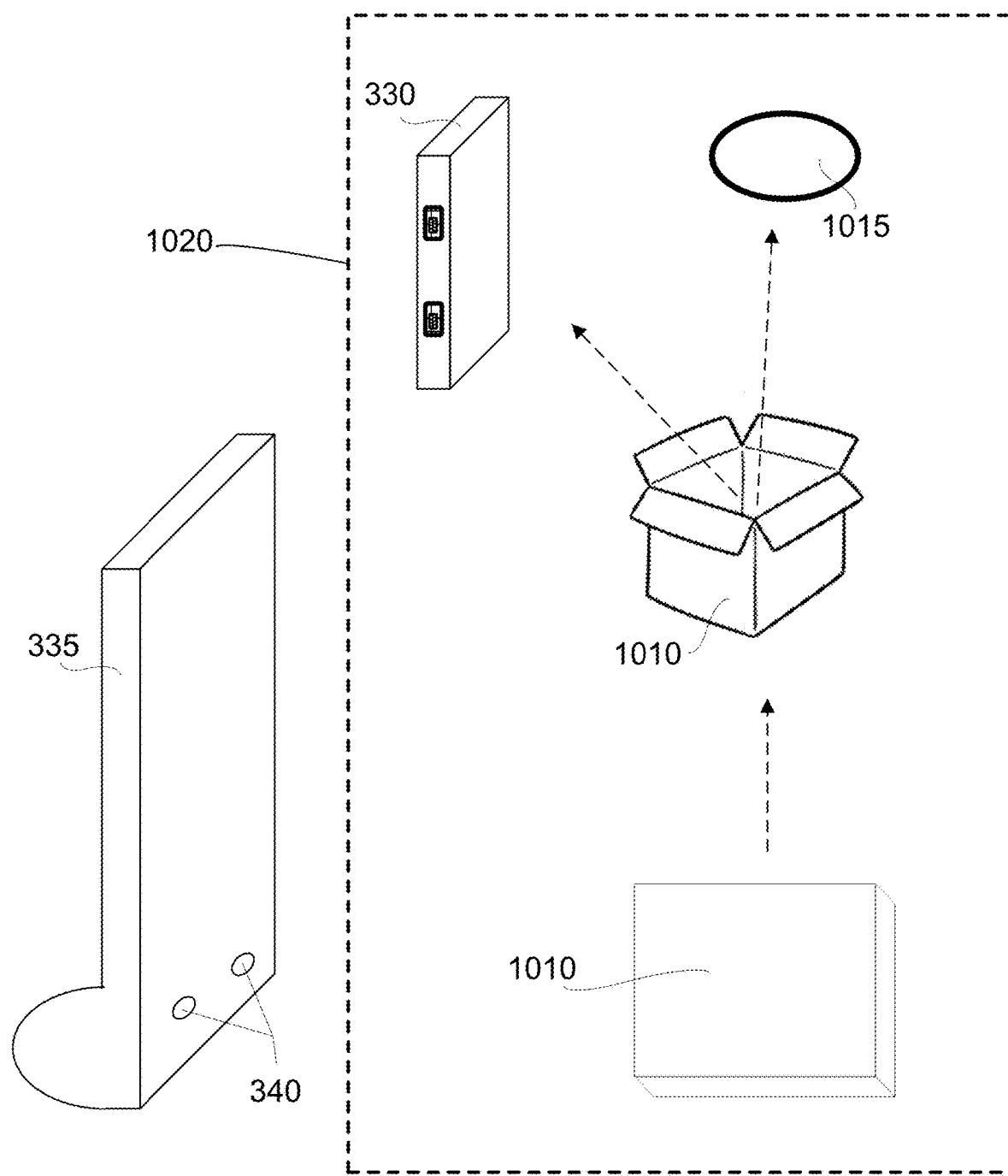
FIG. 10 illustrates within the dashed box the contents or components of a generic adaptor kit to include an adaptor-kit cartridge and an accessory, and also shown is the medical apparatus in its initial state.

The Providing Step (105) includes providing a medical apparatus (335) configured to accept and operationally integrate with an adaptor kit (1020), shown within the dashed box in FIG. 10. Preferably, the medical apparatus (335) is configured to accept and operationally integrate with a plurality of adaptor kits. Each adaptor kit (1020) is figuratively shown in FIG. 10 as contents within a box (1010). The contents include at least one of the adaptor-kit cartridge (330) and includes an accessory (1015) or accessories, preferably a plurality of accessories.

Each adaptor-kit cartridge in the adaptor kit (1020) is configured to be attached to the medical apparatus. Each adaptor-kit cartridge (330) is further configured to operationally integrate with the medical apparatus (335) either alone, or with, or instead of another adaptor-kit cartridge (330); and each adaptor kit (1020) further comprises an accessory (1015) or accessories. In the method (100) and in the alternative method (1300), the adaptor-kit cartridge (330) and the accessory (1015) or accessories are configured to enable a new medical function for the medical apparatus (335).

An adaptor-kit cartridge (330) is a unit specifically designed to adapt the medical apparatus to provide a medical function. The adaptor-kit cartridge (330) and one or more of each of the accessories are necessary to serve the added or different medical function for that adaptor kit (1020). Each accessory (1015) may be a unit included with the adaptor-kit cartridge (330) or may be integrated into the adaptor-kit cartridge (330) so as to enable the new function.

The medical apparatus (335) also preferably contains one or more computer processors to run computer code. Different computer code may be run for the medical apparatus (335) without an adaptor-kit cartridge (330) and run for the adaptor-kit cartridge (330) provided in the adaptor kit (1020).

For the method (100), the Providing Step (105) includes providing the medical apparatus (335) configured to be hand-held (see FIG. 8) by a person (420) for performing an initial-medical function that is either fixed as an initial-medical function or is an initial-medical function that is selected by the user when operating the medical apparatus (335). For the alternative method (1300), the Providing Step (105) involves the initial-state function of the medical apparatus (335), rather than the initial-medical function.

Figure 8:
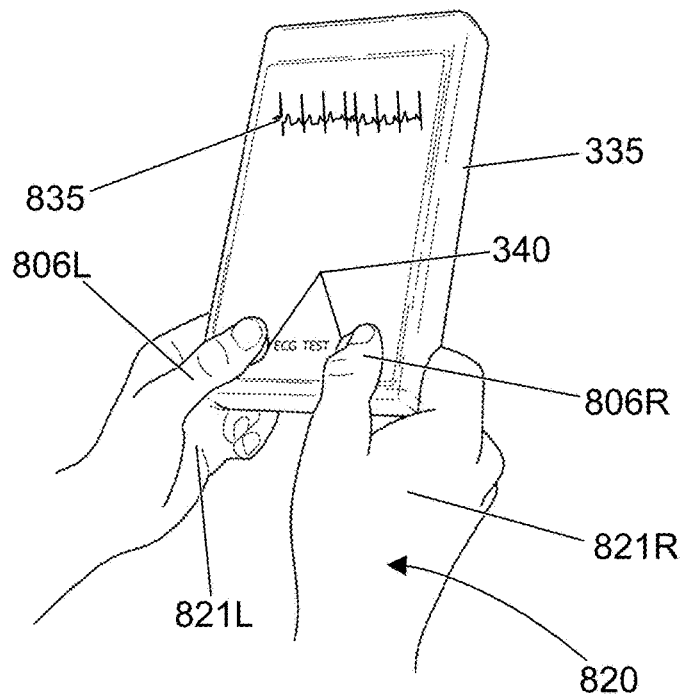
FIG. 8 illustrates use of the medical apparatus with two sensors for a person's thumbs.

For example, a hand-held example is shown in FIG. 8 for a left hand (821L) and a right hand (821R). The initial-medical function may be enabled by the addition of an initial-state cartridge. Preferably, selection of the initial-medical function is automatic when it is enabled by the addition of the initial-state cartridge. The initial-state cartridge preferably includes electronics to uniquely identify the initial-state cartridge and to automatically relay to the medical apparatus the kind of initial-state cartridge and function it enables.

When an adaptor-kit cartridge (330) is provided for functioning with the medical apparatus (335), each adaptor-kit cartridge (330) is preferably a "smart cartridge," which includes an identification chip (ID chip) to verify its authenticity and functionality in concert with the medical apparatus (335). The ID chip includes data accessible by the medical apparatus (335). Such data preferably includes a manufacturing date; an installed date; a used date, and compatibility and functionality with the medical apparatus (335).

In addition, it is preferable that any adaptor-kit cartridge (330) storing disposable electrode pads (300) contains a computer chip that provides a globally unique serial number to enable the medical apparatus (335) to confirm the compatibility of the disposable electrode pad with the cartridge and to enable the medical apparatus (335) to prevent use of an inferior, defective or counterfeit disposable electrode pad and/or cartridge.

In its initial state, the medical apparatus (335) may have an initial-state cartridge attached, or may be configured without the initial-state cartridge. The medical apparatus (335) is configured for performing one or more medical functions or for performing a self-test, or otherwise providing a status of the medical apparatus, providing one or more statuses to the user.

In one embodiment, the one or more functions in the initial state is at least to take an ECG (835) of the person (420). Preferably, there is an option to sequentially perform all of the diagnostic medical functions in a sequential fashion.

A basic initial-medical function is to provide a status of the device (e.g., is the medical apparatus (335) ready to and capable of performing possible functions for which it is configured). For example, displaying a battery status.

When the initial-medical function of the medical apparatus (335) is to take an ECG (835), then the medical apparatus (335) may be used repetitively for taking ECGs on one or more persons and its hand-held configuration makes it relatively easy to use for taking multiple ECGs on one person or on multiple persons.

The one or more medical functions in the initial state of the medical apparatus (335) may be a selectable medical function. For example, the medical apparatus (335) may be configured for measuring blood pressure (1105) within the person (420); measuring blood composition (1110) within the person (420); measuring body temperature (1115) of the person (420); measuring a heart rate (1120) of the person (420); measuring acceleration of a chest (1125) of the person (420) undergoing cardiopulmonary resuscitation (CPR), CPR coaching (1130); and performing automated external defibrillation of the person (420) using the disposable electrode pads, i.e., an AED (1135). In an alternative embodiment, the medical apparatus may default to a medical function in the initial state.

The medical apparatus (335) may be configured to: update the medical device firmware or software (1141); to perform a pre-programmed self-test (1143) of the medical apparatus (335); and to provide status (1144) information about the medical apparatus (335). A user interface to perform or interact with initial-state functions may be native to the medical apparatus (335), or may be available through a different device, such as a smartphone or tablet.

All of the selectable diagnostic medical functions may be elected by the selection of the "ALL" function (1142). When "ALL" is selected, the medical apparatus (335) performs all of the initial-medical functions that are diagnostic, preferably in a pre-selected logical or sequential order. The user interface to perform or interact with initial-medical functions of the medical apparatus (335) may be native to the medical apparatus (335) or the medical apparatus (335) may be configured to make this function available through a different device, such as a smartphone or tablet. Certain non-diagnostic initial-state functions may be performed by the medical apparatus without user interaction, such as providing a device status, checking for software or firmware updates or performing an automated self-test.

The medical apparatus (335) in the Providing Step (105) is further configured to accept and operationally integrate into the medical apparatus (335) contents (i.e. components) in the adaptor kit (1020), preferably configured to accept and operationally integrate one or more of a plurality of adaptor kits enabling different medical functions.

A first content or component of each adaptor kit (1020) comprises an adaptor-kit cartridge (330) configured to be attached to the medical apparatus (335). The attachment of the adaptor-kit cartridge (330) to the medical apparatus (335) operationally integrates the adaptor-kit cartridge (330) into the medical apparatus (335) and together with the accessory or accessories enables the new medical function.

Each adaptor kit (1020) in the Providing Step (105) may further comprise an accessory (1015) or one or more components needed to perform the added or different medical function. Thus, the adaptor-kit cartridge (330) and the accessory (1015) or accessories are configured to support the added or different medical function for the medical apparatus (335). The accessory (1015) may be added to the adaptor-kit cartridge (330) so that it is provided as a single package. Alternatively, accessories may be provided separately as consumables and so may be provided as a supplement to the adaptor kit (1020).

The optional Using Step (110) is using the medical apparatus to perform the initial-medical function, or in the case of the alternative method (1300), to perform the initial-state function. The initial-medical function may be one that is fixed or built-in as the initial-medical function or is an initial-medical function that is selected by a user when operating the medical apparatus (335), or an automated function provided by the medical apparatus (335). The initial-medical function may be preprogrammed in medical apparatus (335), which may have multi-function capabilities.

One such medical function capability of the initial-state is preferably configured for taking measurements of sound and/or bio-electrical signals from the bare skin (820) of the person (420) using the at least two separated sensors (340) when placed on the bare skin (820) of the person (420).

The at least two separated sensors (340) may be configured to produce a low electric current between them and then measure the results of the current flow on the bare skin (820). Sensors for making these measurements are well known and are possible by detecting the body's electrical signals emanating from the person in a manner which is similar single-lead ECGs.

In the method (100), the Choosing Step (115) is choosing the initial-medical function, or in the alternative method (1300) is choosing the initial-state function, from one or more in the group consisting of: taking an ECG (835) of the person (420); measuring blood pressure (1105) within the person (420); measuring blood composition (1110) within the person (420); measuring body temperature (1115) of the person (420); measuring a heart rate (1120) of the person (420); measuring acceleration of a chest (1125) of the person (420) undergoing cardiopulmonary resuscitation (CPR coaching (1130)) in delivery of a medical function; performing automated external defibrillation of the person; installing a firmware or software update (1141) to the medical apparatus (335); performing a pre-programmed self-test (1143) of the medical apparatus (335); and providing status (1144) information about the medical apparatus (335). Certain initial-medical functions may be chosen by a user through a user-interface, automatically chosen by the medical apparatus, or both.

When enabled as an initial-medical function, coaching involves advice using a speaker (1140), or other user interface (e.g., a screen) on the medical apparatus (335) or alternatively on a connected device, such as a smart phone.

The Choosing Step (115) is one that permits the person (420) to select a medical function preprogrammed and enabled for the medical apparatus (335). Preferably, the initial-medical function, or the initial-state function, may be selected from an option menu displayed on the medical apparatus (335) or screen connected thereto.

For the method (100), the accessories necessary to perform the initial-medical function are provided with the medical apparatus (335).

For example, the function of measuring acceleration of a chest (1125) of the person (420) undergoing cardiopulmonary resuscitation (CPR) may be enabled by an inertial measurement unit (IMU) or an accelerometer within or attached to the medical apparatus (335). An IMU integrates multi-axes, accelerometers, gyroscopes, and other sensors to provide estimation of an object's orientation in space. Preferably, the inertial measurement unit measures 9 axes: 3 axes for acceleration, 3 for gyroscope, and 3 for magnetometer. Measurements of acceleration, angular rate, and attitude are typical data outputs. IMU inertial sensors are commonly used in dynamic motion measurements, payload platform stabilization, and antenna and camera pointing applications.

Figure 11:
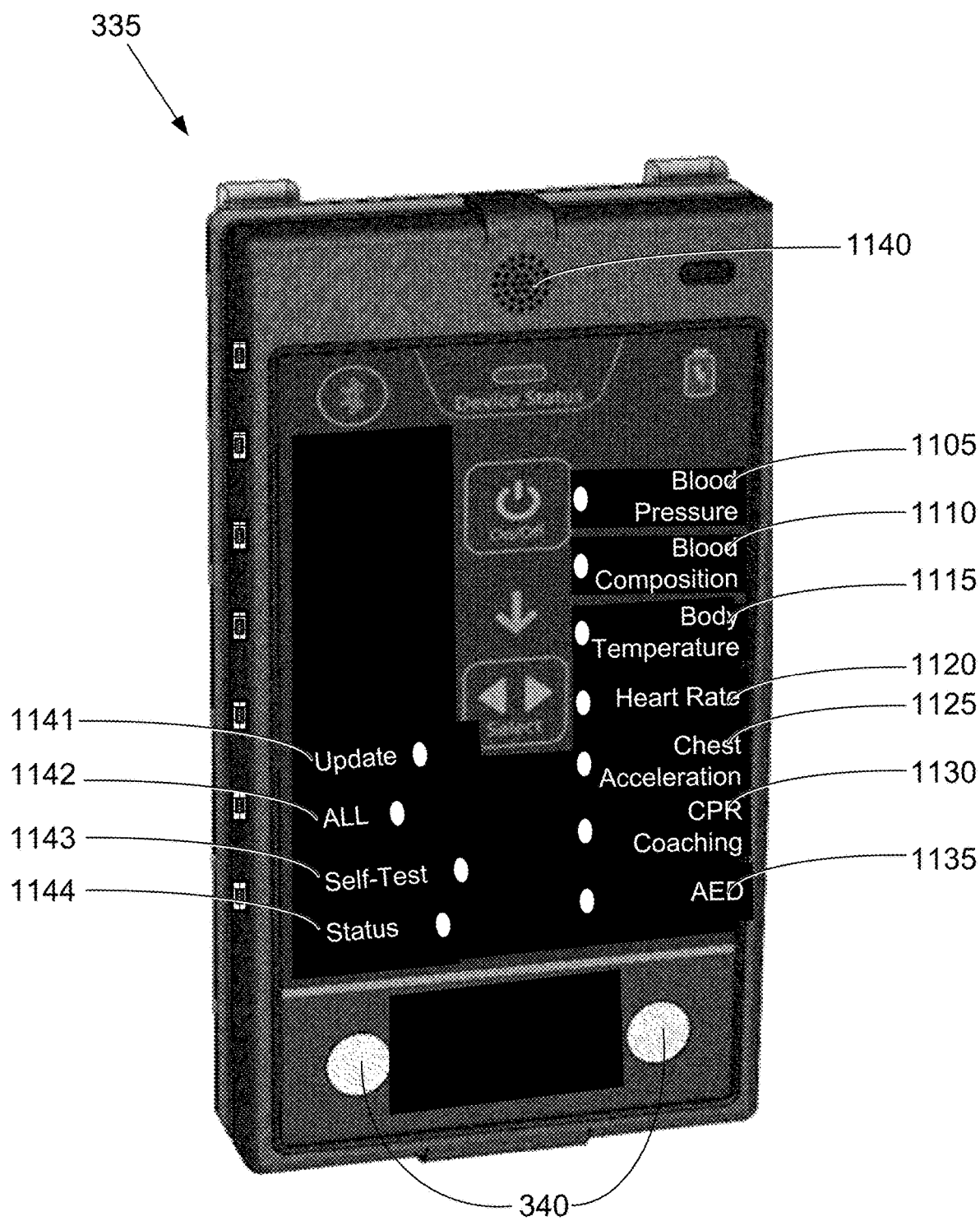
FIG. 11 illustrates a configuration of the medical apparatus that enables a user to select one or more of the optional initial-medical functions of the medical apparatus.

As shown in FIG. 11, all of the selectable diagnostic medical functions may be elected by the selection of the "ALL" function. When "ALL" is selected, the medical apparatus (335) performs all of the selectable diagnostic medical functions, preferably in a pre-selected logical or sequential order. In an alternative embodiment, the selection of certain functions, such as self-tests, firmware or software updates, or providing medical apparatus status may be automated.

The Selecting Step (120) includes optional steps in selecting the initial-medical function(s) or initial-state functions. Examples include taking an ECG (835) of the person (420), identifying a need for an ECG (835) from the person (420), the person (420) having bare skin (820) accessible to at least two separated sensors (340), the at least two separated sensors (340) operationally connected to the medical apparatus (335); and touching the bare skin (820) to the at least two separated sensors (340). The bare skin (820) may be on a person's chest or arm, or when the ECG (835) is desired, the bare skin (820) is preferably on the person's fingers, as shown in FIG. 8.

The Configuring Step (125) is configuring the at least two separated sensors (340) to be functional when the person (420) places a finger on each of the separated sensors, for example a left-hand thumb (806L) and a right-hand thumb (806R). Preferably, the medical apparatus (335) is configured to have the person (420) place a finger from each hand on one of the at least two separated sensors (340).

The Supplying Step (130) is an optional step of providing the medical apparatus (335) with multiple leads (345) for use in taking the ECG (835). Multiple leads (345) are superior to a single-lead because they offer multiple perspectives of the heart's activity from different angles.

The multiple leads (345) may be generated by using single wires with an attachment end that is placed on the person (420) or configured with one or more connector ends for electrical connection to the medical apparatus (335). These may also be multicore wires or cables that separate at one end for multiple attachments to the bare skin (820) of the person and have one or more connector ends for electrical connection to the medical apparatus (335).

Preferably, the multiple leads (345) are provided in a multicore wire that has multiple insulated conductors within a single jacketed cable as shown in FIG. 3. Preferably, the multiple leads (345) are configured to support 6, 12 or 15 lead ECGs. Additionally, the medical apparatus (335) may be configured to take the person's body temperature using the at least two separated sensors (340) or the multiple leads (345).

Modification Enabling New Medical Function

The method (100) and the alternative method (1300) both identify at least three specific adaptor kits in order to change or add one or more medical functions to the medical apparatus (335). Providing the wAED adaptor kit, the AED adaptor kit (610) and the ECG adaptor kit (1200) are optional steps in the method (100). Providing the wAED adaptor kit is a required step in the alternative method (1300).

New Medical Function—AED

The AED Adaptor Step (205) further includes a step of providing an AED adaptor kit (610). The AED adaptor kit (610), shown within the dashed box in FIG. 6, comprises: an AED cartridge (630); and disposable electrode pads (300), which are the required accessories for this AED adaptor kit (610). Preferably, there are at least two disposable electrode pads.

The AED adaptor kit (610) is configured to enable the medical apparatus (335) to perform a first new medical function of an automated external defibrillator (AED). The AED adaptor kit (610) comprises: an AED cartridge (630) and disposable electrode pads (300).

The AED Connecting Step (215) includes providing an AED adaptor kit (610). The AED adaptor kit (610) is configured to enable the medical apparatus (335) to perform a second new medical function of a reusable non-wearable automated external defibrillator. This second new medical function is referred to herein as an AED.

A Storage Step (220) is configuring the AED cartridge (630) to store each of the disposable electrode pads (300) while each such disposable electrode pad is electrically connected to AED cartridge (630).

The AED cartridge (630) may be single-use. Each of the disposable electrode pads is (300) is preferably pre-wired to the AED cartridge (630) and need only be unpacked from the AED cartridge (630) and applied to the person (420) to enable defibrillation.

Added steps enabling use of the AED adaptor kit (610) include placing on the person (420) a left-disposable-electrode pad (300L) and a right-disposable-electrode pad (300R) from the plurality of AED disposable electrode pads. The designations "left" and "right" are for description purposes only because there would typically be no physical or structural distinction between them.

Figure 9:
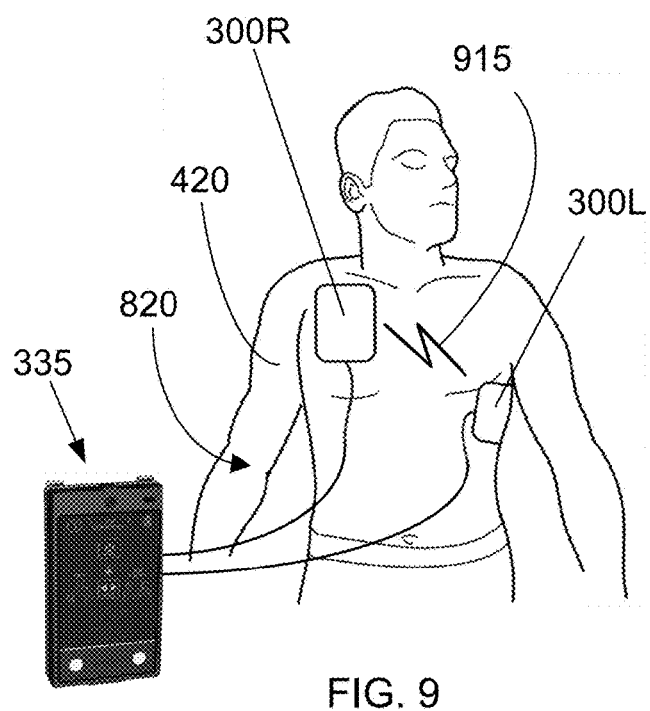
FIG. 9 illustrates use of the medical apparatus as an AED.

Preferable placement of the disposable electrode pads (300) is generally as shown in FIG. 9. Each of the disposable electrode pads (300) is attached to bare skin (820) at designated areas (which are preferably at center chest and back, a patient's right upper quadrant under the collar bone and a patient's left middle side, or any other place that facilitates a therapeutic charge (915) delivered for defibrillation of the heart). Placement on the front and back of the person (420) may be used in accordance with standard practices sometimes relating to the age of the person undergoing defibrillation.

The AED Connecting Step (215) optionally includes a step of connecting the AED cartridge (630) to the medical apparatus (335) to enable its operation; and placing on the person (420) two of the disposable electrode pads.

Example of an AED Adaptor Kit

An example of an AED adaptor kit includes an AED cartridge (630) that also stores at least two of the disposable electrode pads (300) that are directly wired to the AED cartridge (630). Once the AED cartridge (630) is connected to the medical apparatus (335), the disposable electrode pads (300) are also connected to the medical apparatus (335).

In this example, to utilize the AED adaptor kit (610), a user opens the AED cartridge (630) to access two disposable electrode pads by taking off a back cover or peeling off a seal on the AED cartridge (630). Then the user removes the disposable electrode pads (300) and applies them to the person (420). The disposable electrode pads (300) are electrically connected to the AED cartridge (630).

In other embodiments, replacement disposable electrode pads are provided and these simply plug into the AED cartridge (630) or plug into the medical apparatus (335). When used in combination with the AED adaptor kit (610), the medical apparatus (335) contains the necessary electronics to provide a therapeutic charge (915) for defibrillation.

Optionally, the AED cartridge (630) employs an external battery to ensure that adequate power is available for defibrillation using the disposable electrode pads (300).

Optionally, the medical apparatus (335) offers a lower power sleep mode to conserve power, waking up from low power mode to enter an initial-state.

New Medical Function—wAED

The wAED Adaptor Step (221) includes providing a wAED adaptor kit (710), the wAED adaptor kit (710) is configured to enable the medical apparatus (335) to perform a first new medical function of a wearable automated external defibrillator (wAED), the wAED adaptor kit comprises a wAED cartridge (730) configured to attach to, and operationally integrate with, the medical apparatus (335); and disposable electrode pads (300). Optional steps in addition to the wAED Adaptor Step (221) are the wAED Harness Step (222) and the wAED Implementation Step (223).

The wAED Harness Step (222) requires the wAED adaptor kit (710) to include a harness (405) and includes a step of attaching the disposable electrode pads (300) to the person (420).

The wAED Implementation Step (223) adds additional steps of connecting the wAED cartridge (730) to the medical apparatus (335); and attaching the disposable electrode pads (300) to the person (420).

An alternative method (1300) of using the medical apparatus (335) includes a wAED Providing Step (1305) and a wAED Attaching Step (1310), which unlike for the method (100), the wAED Adaptor Step (221) in the alternative method (1300) is a required step. The alternative method (1300) provides the medical apparatus (335) and the alternative method (1300) requires providing the wAED adaptor kit (710) so that the medical apparatus (335) can be immediately converted to a wAED. This is the same as the wAED Adaptor Step (221) for the method (100), except that for the alternative method (1300), the medical apparatus (335) is configured prior to alteration to perform an initial-state function, rather than an initial-medical function. The difference is that the initial-state function is broader and includes medical apparatus (335) administrative upkeep tasks to support medical functions in addition to any medical functions themselves.

Figure 7:
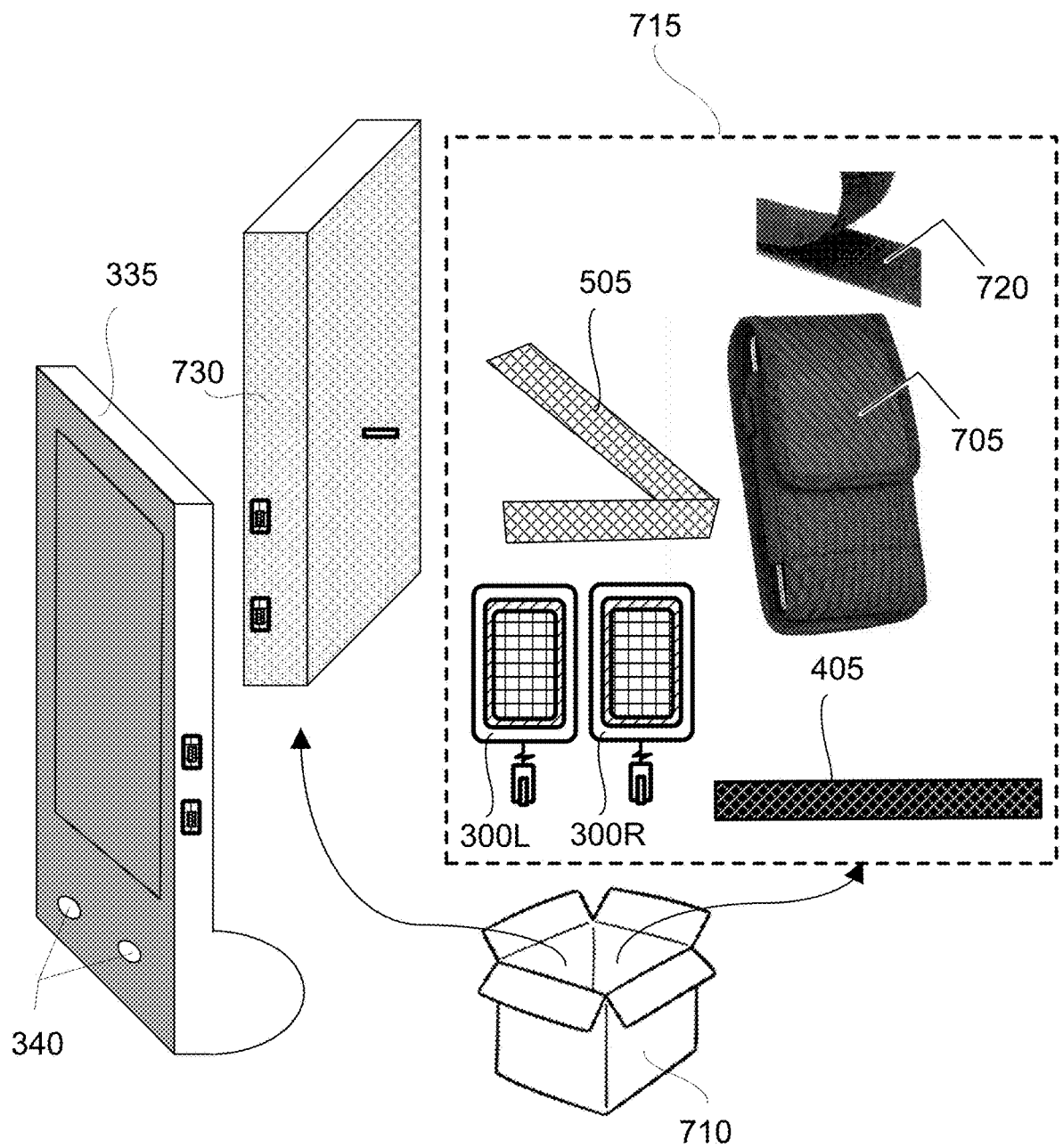
FIG. 7 illustrates contents or components of a first adaptor kit for the wAED, including a harness.

FIG. 7 illustrates contents or components of a wAED adaptor kit (710) to enable altering the medical apparatus (335) to perform the new medical function of a wearable automated external defibrillator. The wAED adaptor kit (710) includes wAED cartridge (730) and a harness (405) and may optionally include disposable electrode pads (300).

The wAED cartridge (730) attaches to, and operationally integrates with, the medical apparatus (335). In a preferred embodiment, the medical apparatus (335) allows the person (420), that is the patient, to take an ECG preferably using four electrodes two of which are the disposable electrode pads (300) (also known as patches). In this implementation, the other two electrodes are the at least two separated sensors (340) on the medical apparatus (335). The at least two separated sensors (340) are surface electrodes or tabs that are accessible to the fingers or hands of the user on an external surface of the medical apparatus (335). Finger examples are shown in FIG. 8 as a left-hand thumb (806L) and a right-hand thumb (806R). Alternatively, additional surface electrodes may be on the wAED cartridge (730), which may be laid on the bare skin (820) of the person (420).

The wAED adaptor kit (710) may include a harness (405). When included, the harness (405) is configured to be worn by the person (420) and may route wires from the disposable wAED electrode pads to the medical apparatus (335). The harness (405) is an accessory in the wAED adaptor kit (710) that is defined herein to include a belt, as shown in FIG. 4; a shoulder rig (505) as shown in FIG. 5 or as in any other shoulder belting arrangement; a clip attachment (705) usable on the clothing or belt of a person; a hook-and-loop strip (720) attached or attachable to the person or to the person's belt or to other clothing worn by the person; and any other device-holding mechanism for use on a person or a person's clothing.

When included in the wAED adaptor kit (710), the harness (405) preferably includes a connecting wire (350) that may be embedded in the harness (405), a connecting wire (350) may also be provided as a separate or backup accessory. In either case, the harness (405) provides a convenient organizing function for the wires to establish an electrical connection between the disposable electrode pads (300) and the wAED cartridge (730) and/or the medical apparatus (335).

Harness Examples

Figure 5:
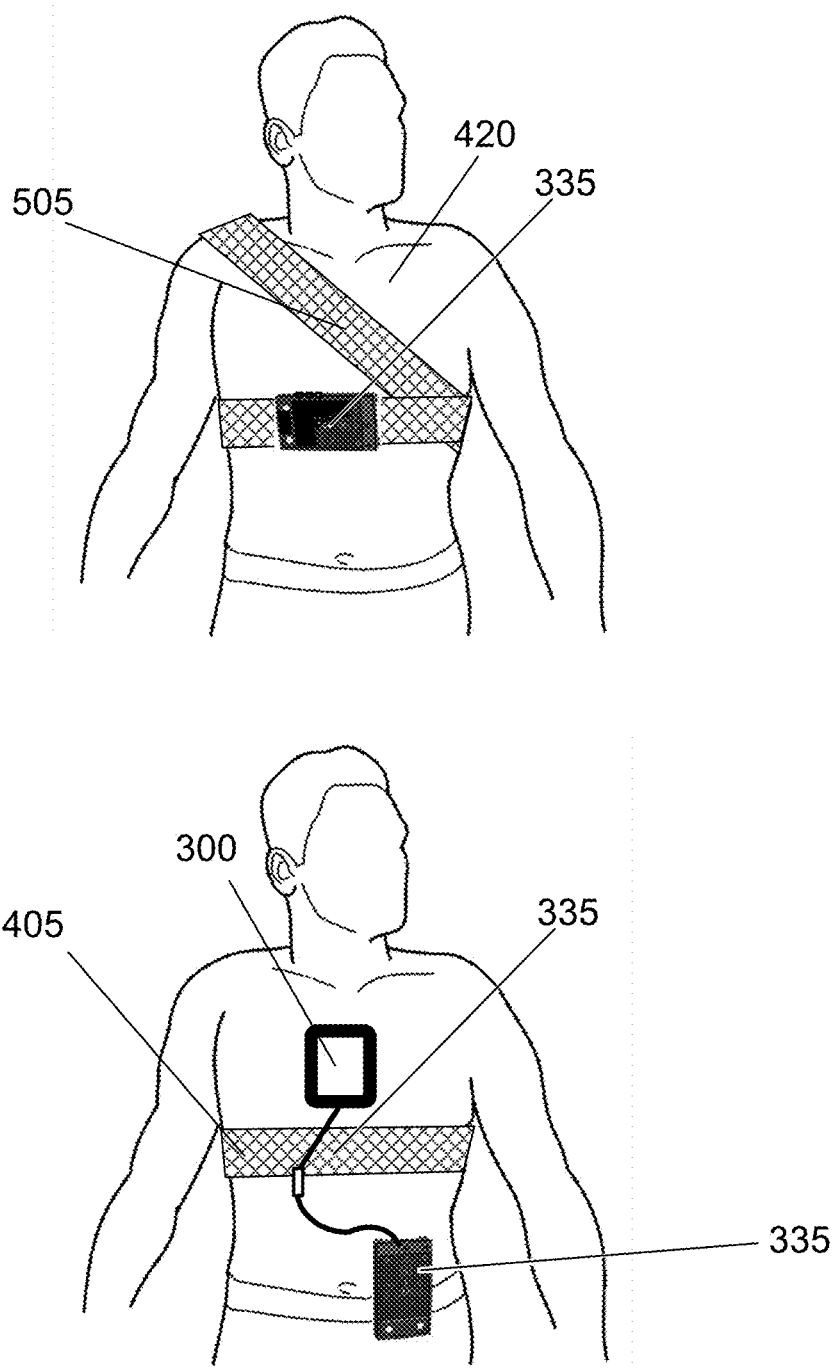
FIG. 5 shows two frontal views of a person with alternative configurations of the harness and two different locations for attachment of a medical apparatus connected to a wAED cartridge.

Examples of securing the harness (405) to the person (420) are illustrated in FIG. 4 and FIG. 5 showing a harness (405) and a harness that is a shoulder rig (505) that is supported by one shoulder. Alternative examples in FIG. 4 and FIG. 5 show the harness (405) surrounding the person's waist or chest. The lower illustration of the person without a shoulder rig (505) has an arrangement of one of the disposable electrode pads (300) on the front and one of the disposable electrode pads (300) on the back (not shown) of the person (420).

wAED Accessories

In FIG. 7, the rectangular dashed box illustrates accessories, including suggested alternative embodiments of the harness (405), as illustrated in FIGS. 4, 5 and 7. These alternative embodiments of the harness (405) are referred to herein as harness (405), shoulder rig (505), clip attachment (705), and hook-and-loop strip (720).

One of these alternative embodiments of the harness (405) is preferably included in the wAED adaptor kit (710). Optionally, the harness (405) in any embodiment may incorporate the wAED cartridge (730), so that once the harness (405) is plugged into the medical apparatus (335), no separate wAED cartridge is required. For this implementation, the wAED cartridge (730) is physically available within one of these alternative embodiments.

Preferably, each of the disposable electrode pads (300) includes an electrical wire (319) that terminates in a plug (320). The plug (320) is configured to attach to a mating plug (325) on a connecting wire (350) to the wAED cartridge (730) or to the medical apparatus (335). Alternatively, the electrical wire (319) or connecting wire (350) may run through the harness (405). The plugs may be male or female on one or the other end of the wire as long as they are configured to mate with the connecting plug. The connecting wire (350) is optionally part of the wAED adaptor kit (710) or may be provided as a separate component.

Each of the disposable electrode pads (300) and any wires that are riveted or otherwise permanently attached to each of the disposable electrode pads (300) are configured to be disposable after one or more uses. Preferably, the adaptor-kit cartridge (330) that is used in the method (100) and used in the alternative method (1300) is configured for reuse without any need for replacement after a first or any subsequent use for the new medical purpose.

The harness (405) is preferably configured to be reusable but replaceable after it is worn out. In one embodiment, the clip attachment (705) is a clip on the back of the wAED cartridge (730).

The harness (405) is further configured for facilitation of a wired connection of each of the disposable electrode pads (300) to the wAED cartridge (730). It is preferred that there be at least two such wired connections in a typical use of the wAED (one for each pad): a connection from a left-disposable-electrode pad (300L) and one from a right-disposable-electrode pad (300R). The right and left designations are only for convenience of describing them because there is typically no other distinguishing feature between a left and right disposable-electrode pad.

Such facilitation from the harness (405) may preferably include connecting with each electrical wire (319) from two wAED disposable electrode pads used on a person (420) in a typical implementation using the wAED adaptor kit (710), as shown in FIG. 9. The harness (405) may be configured to comfortably conceal and hold the medical apparatus (335) with the wAED cartridge (730) attached.

Also, such facilitation may include concealing and routing each connecting wire (350), each plug (320), and each mating plug (325) from each of the disposable electrode pads (300) to the wAED cartridge (730). A hook and loop fastener or a belt clip on the cartridge or medical apparatus are examples of tools to hold the medical apparatus (335) with the wAED cartridge (730) attached. The medical apparatus (335) with the wAED cartridge (730) attached may also be stored in the person's clothing or carried in a person's pocket. When a mating pair of plug-in connectors is used: one on each end of the connecting wire (350) from the wAED cartridge (730) and one on the electrical wire (319) connecting to each of the disposable electrode pads (300).

These optional steps in the method (100) and also in the alternative method (1300) are referred to in FIG. 2 as an AED Adaptor Step (205), an AED Connecting Step (215), a Storage Step (220), a wAED Adaptor Step (221), a wAED Harness Step (222), a wAED Implementation Step (223), and an ECG Adaptor Step (225).

Figure 6:
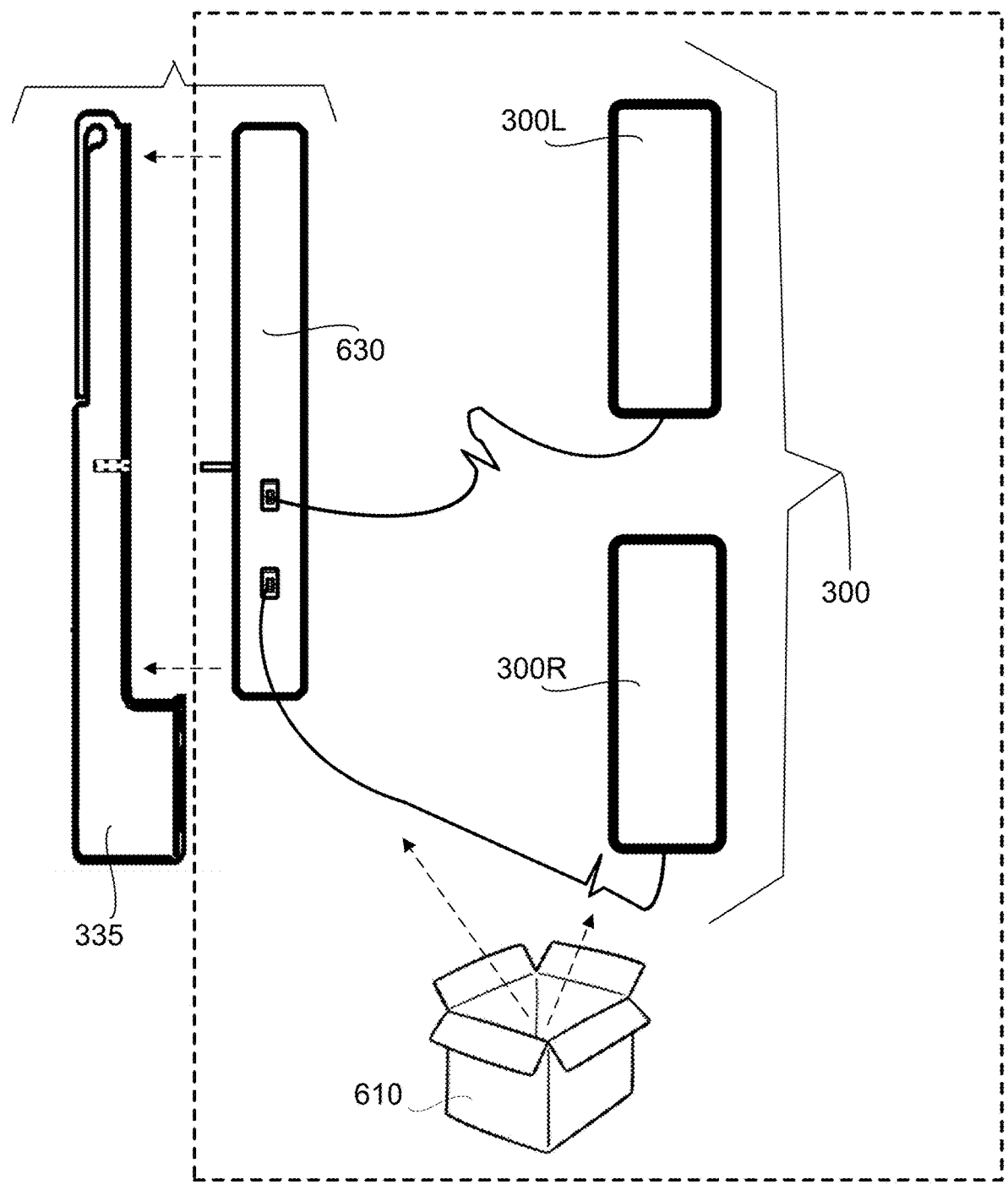
FIG. 6 illustrates the contents or minimum necessary components of an AED adaptor kit (within a dashed box) and also an exploded side view of the medical apparatus and AED cartridge and a top view of two disposable electrode pads.

The AED Adaptor Step (205) includes providing an AED adaptor kit (610). The AED adaptor kit (610) is configured to enable the medical apparatus (335) to perform a first new medical function of a reusable non-wearable automated external defibrillator. The reusable non-wearable automated external defibrillator is referred to herein as an AED and is shown in FIG. 6

The AED adaptor kit (610) includes an AED cartridge (630) and an AED accessory (715). There is preferably at least one accessory in the AED adaptor kit (610), including at least two of the disposable electrode pads (300), which may be referred to herein as a plurality of disposable electrode pads. The disposable electrode pads (300) may alternatively be provided in packaging supplemental to the AED adaptor kit (610). Each of the disposable electrode pads (300) is exemplified in FIG. 3 within the dashed box.

For the method (100), the optional Using Step (110) includes using the medical apparatus (335) to perform at least one initial-medical function. For the alternative method, the optional Using Step (110) includes using the medical apparatus (335) to perform at least one initial-state function The use of the medical apparatus (335) may be pre-programmed, allowing such use to be automated, or may involve interaction with a medical apparatus operator through a user interface.

The present disclosure teaches a preferable configuration for the disposable electrode pads (300) that enables daily use by the person (420). Preferably, each of the disposable electrode pads (300) that is disclosed herein is stored in a sealed package. Preferably, each of the disposable electrode pads (300) would be sealed separately, but a plurality of such disposable electrode pads may also be sealed together in the same package. Preferably, the disposable electrode pads (300) would be purchased (via prescription in some countries) in a box with a large number of sealed patches. Each of the disposable electrode pads (300) is configured to be worn throughout the day or night. FIG. 3 illustrates a bottom view (sticky side up) of a preferred disposable electrode pad as it might look when taken out of a package prior to placement on the bare skin (820) of a person (420).

While similar to electrode pads used by public access automated external defibrillators on the market today, each of the disposable electrode pads (300) is different in that each of the disposable electrode pads (300) is configured to be worn throughout the day, similar to how one might where a dermal patch designed to deliver medication, like a nicotine patch used as a substitute for cigarette smoking. Like all dermal patches, each of the disposable electrode pads (300) is preferably not configured for reuse once removed from the bare skin (820) of the person (420), either on the person (420) or on another patient. Depending on the embodiment of the harness, each of the disposable electrode pads (300) is configured may be placed under, or partially under, the harness (405) at least as often as the person (420) removes or dons the harness (405).

Each of the disposable electrode pads (300), like a dermal patch, is essentially a stand-alone dermal sticker. Each of the disposable electrode pads (300) taught herein is preferably not the usual AED electrode pad because each of the disposable electrode pads (300) is configured to be worn for long durations, e.g. preferably up to a full day or longer.

Each of the disposable electrode pads (300) is exemplified in FIG. 3. Each of the disposable electrode pads (300) is typically attached to a connecting wire (350) that is the interface between the person and the adaptor-kit cartridge (330), enabling the device to analyze the heart's rhythm and deliver electric charge to restore standard heartbeat patterns.

The disposable electrode pads (300) preferably include: a skin adhesive (305) (e.g., hydrogel or pressure sensitive adhesive); and one or more conductive elements (315) (e.g., hydrogel, carbon-loaded vinyl, tin, or silver). Preferably, each of the disposable electrode pads (300) includes: an optimized formulation of hydrogel that serves as a conductive agent and an aid in adhering each of the disposable electrode pads (300) to the person's skin. Preferably, the skin adhesive (305) is a pressure sensitive adhesive that supports day-long adhesion and helps retain electrical conductivity while being worn by the person (420).

Preferably, each of the disposable electrode pads (300) is the same size. Pad size would preferably comply with the International Electrotechnical Commission (IEC) standard for Medical electrical equipment—Part 2-4: Particular requirements for the basic safety and essential performance of cardiac defibrillators IEC 60601-2-4. This IEC standard sets forth requirements for the basic safety and essential performance of cardiac defibrillators. According to this IEC standard, the minimum area of each of the electrodes, one of which is part of, or attached, to each patch, must be 50 cm2 for adult external use and 15 cm2 for pediatric external use. Together, the total active (gel) area for two disposable electrode pads would be at least 150 cm2 for adults and 45 cm2 for children, but preferably would have a larger active gel area.

The AED Connecting Step (215) includes multiple actions comprising: connecting the AED cartridge (630) to the medical apparatus (335) to enable its operation; and placing on the person (420) two of the disposable electrode pads.

An example of a typical placement of two of the disposable electrode pads (300) on an adult is illustrated in FIG. 4. A left-disposable-electrode pad (300L) and a right-disposable-electrode pad (300R) are shown in FIG. 4.

The method (100) of using the medical apparatus (335) optionally includes the AED Connecting Step (215), which adds optional steps to the AED Adaptor Step (205). The added steps include attaching the AED cartridge (630) to the medical apparatus (335); adhering two disposable electrode pads to the person (420); and electrically connecting the disposable electrode pads (300) to the medical apparatus (335) either directly or through the AED cartridge (630).

The harness (405) is further configured to hold the medical apparatus (335) with the wAED cartridge (730) attached thereto. As with all adaptor-kit cartridges (330), the wAED cartridge (730) operationally integrates with the medical apparatus (335). A hook and loop fastener, a clip attachment (705), a pocket or a slot are potential attachment mechanisms.

The AED Connecting Step (215) further includes a step of securing the harness (405) to the person (420). Examples of the harness (405) are illustrated in FIG. 4 and FIG. 5 showing a harness (405) and a shoulder rig (505) that is supported by one shoulder. As an example, the harness (405) may surround the person's waist or chest, as illustrated in FIG. 4 and FIG. 5, respectively.

To extend the life of the wAED, an external battery is optionally embedded in the harness (405) or harness (405). Alternatively, the external battery may be electrically connected but detached and apart from the harness (405). Alternatively, a battery may be present in the wAED cartridge (730) that connects to the harness (405). The battery may be rechargeable or non-rechargeable.

Detecting and alerting the person (420) when any disposable electrode pads (300), also referred to as a patch, should be changed: Preferably, a timely recommendation to the person (420) to change each of the disposable electrode pads (300) is initiated by measuring the resistance between the left-disposable-electrode pad (300L) and the right-disposable-electrode pad (300R). When the resistance drops to a pre-determined threshold, the person (420) is alerted to change the patches. Software within the medical apparatus (335) or within the wAED cartridge (730) may be programmed to use a timer to alert the person (420) when it is recommended to replace the disposable electrode pads.

Preferably, the wAED cartridge (730) interfaces with the medical apparatus (335) and the medical apparatus (335) includes a wireless communication capability to provide near-real time telemetry of patient conditions. Such telemetry may include a speaker (1140) and screen or user interface. Preferably, the screen, speaker, or user interface includes a visual or audible alert and ability to cancel before an electric charge is delivered from the medical apparatus (335) with the wAED cartridge (730) attached. Preferably, telemetry is also used for analysis of the person's heart activity and to predict heart failure.

Preferably, the medical apparatus (335) with the wAED cartridge (730) attached is configured to wirelessly communicate with a smartphone or a smart tablet, for example using BLUETOOTH. The medical apparatus (335) with the wAED cartridge (730) attached may have cellular telephone capability. Preferably, the medical apparatus (335) with the wAED cartridge (730) attached includes a speaker (1140).

Preferably, the medical apparatus (335) with the wAED cartridge (730) attached has a cellular or a wi-fi chip to transmit ECG telemetry directly to a provider or to the cloud. Optionally, the medical apparatus (335) with the wAED cartridge (730) attached tethers to a smart device to enable telemetry transmission. Optionally, the medical apparatus (335) with the wAED cartridge (730) attached has a video interface. The medical apparatus (335) with the wAED cartridge (730) attached optionally has a non-video interface and is configured to utilize a video and speaker from a smart device, such as a cell phone (i.e., smartphone).

Third New Medical Function

Figure 12:
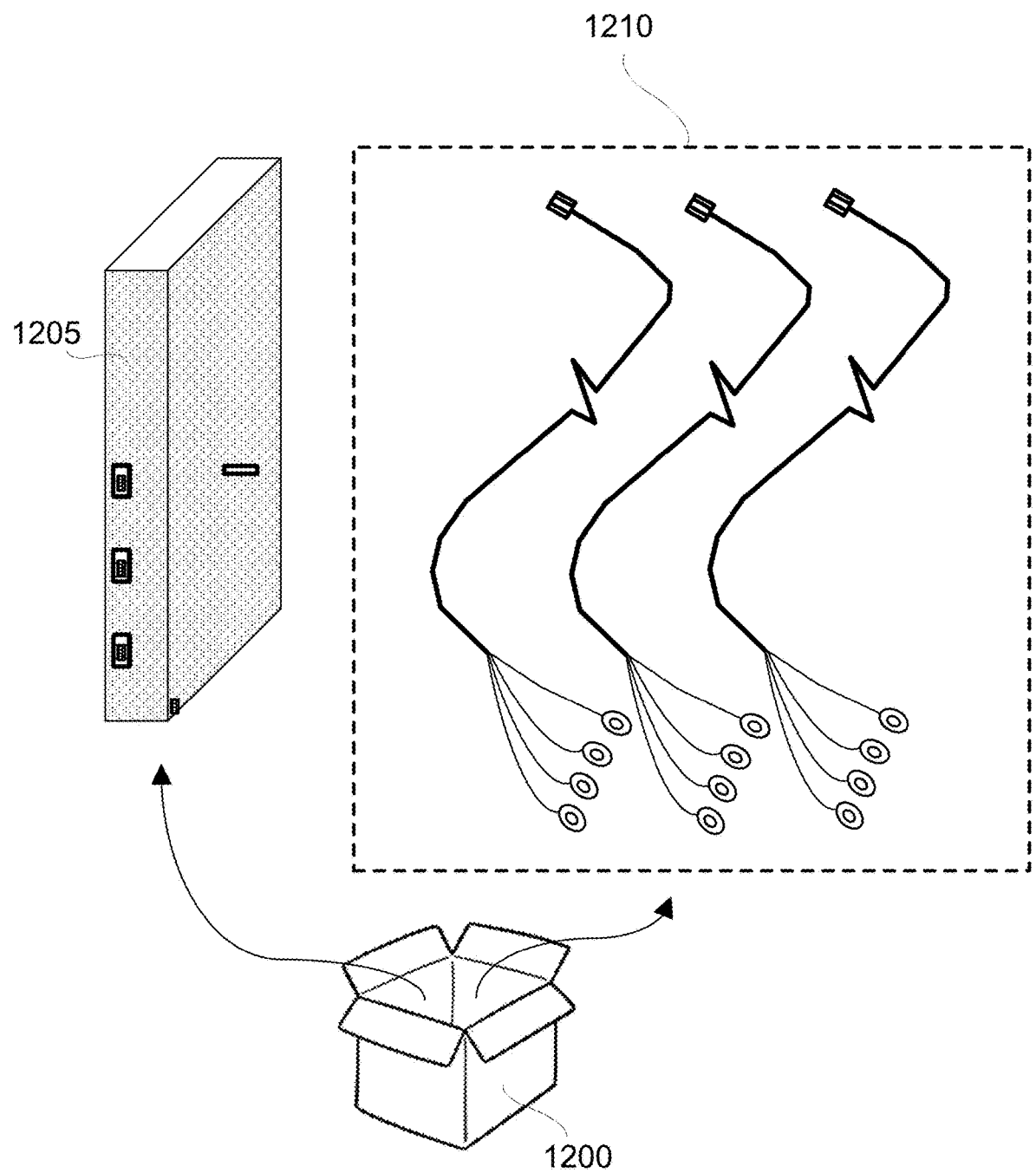
FIG. 12 illustrates the contents of an ECG adaptor kit for performing an electrocardiogram.

The ECG Adaptor Step (225) includes providing an ECG adaptor kit (1200), the third adaptor kit configured to enable the medical apparatus (335) to perform a third new medical function of taking an electrocardiogram (ECG), the third adaptor kit comprises: an ECG cartridge (1205); and a plurality of sensors (1210), preferably at least 12 sensors, configured to measure the magnitude and direction of electrical currents in a heart during each heartbeat. The plurality of sensors (1210) is shown within the dashed box in FIG. 12.

Industrial Applicability

The invention has application to the emergency medical industry.

What is claimed is:

1. A method of using a medical apparatus, the method comprising the steps of:
providing the medical apparatus configured to perform an initial-state function;
the medical apparatus further configured to be modified by an addition of contents of one or more adaptor kits to perform a new medical function;
the medical apparatus further configured to be handheld by a person; and to accept and operationally integrate into the medical apparatus, the contents in a wearable automated external defibrillator adaptor kit (a wAED adaptor kit); the contents of the wAED adaptor kit comprising a wAED cartridge and at least one accessory;
providing a harness and disposable electrode pads, wherein the harness is configured: to be secured on the person and attached to the medical apparatus; and
providing the wAED adaptor kit, wherein the wAED cartridge and the harness are configured to be accepted and to be operationally integrated into the medical apparatus and further configured to enable the medical apparatus to perform a new medical function of a wearable automated external defibrillator (wAED).

2. The method of claim 1, further comprising the steps of: attaching the wAED cartridge to the medical apparatus; adhering two disposable electrode pads to the person; and electrically connecting the disposable electrode pads to the medical apparatus.

* * * * *